US010746729B2

(12) United States Patent
De La Rosa et al.

(10) Patent No.: US 10,746,729 B2
(45) Date of Patent: Aug. 18, 2020

(54) BIOMARKERS FOR DETERMINING THE CLINICAL RESPONSE TO CELL THERAPY

(71) Applicant: TiGenix, S.A.U., Tres Cantos (ES)

(72) Inventors: Olga De La Rosa, Tres Cantos (ES); Wilfried Dalemans, Leuven (BE)

(73) Assignee: TIGENIX, S.A.U., Tres Cantos (Madrid) (ES)

( * ) Notice: Subject to any disclaimer, the term of this patent is extended or adjusted under 35 U.S.C. 154(b) by 184 days.

(21) Appl. No.: 15/568,563

(22) PCT Filed: Apr. 25, 2016

(86) PCT No.: PCT/EP2016/059196
§ 371 (c)(1),
(2) Date: Oct. 23, 2017

(87) PCT Pub. No.: WO2016/170187
PCT Pub. Date: Oct. 27, 2016

(65) Prior Publication Data
US 2018/0156785 A1 Jun. 7, 2018

(30) Foreign Application Priority Data

Apr. 24, 2015 (EP) .................................. 15382206

(51) Int. Cl.
*G01N 33/50* (2006.01)
*A61K 35/28* (2015.01)
*G01N 33/68* (2006.01)

(52) U.S. Cl.
CPC ......... *G01N 33/5094* (2013.01); *A61K 35/28* (2013.01); *G01N 33/6893* (2013.01); *G01N 2333/705* (2013.01); *G01N 2333/70539* (2013.01); *G01N 2333/70578* (2013.01); *G01N 2333/715* (2013.01); *G01N 2333/7155* (2013.01); *G01N 2333/7156* (2013.01); *G01N 2800/52* (2013.01)

(58) Field of Classification Search
None
See application file for complete search history.

(56) References Cited

U.S. PATENT DOCUMENTS

2008/0095749 A1* 4/2008 Aggarwal .............. A61K 35/28
424/93.7

FOREIGN PATENT DOCUMENTS

WO  2014140362 A2  9/2014
WO  WO 14/207679  * 12/2014 .......... C12N 5/0775

OTHER PUBLICATIONS

"History of Changes for Study: NCT01663116: Cx611-0101, eASCs Intravenous Administration to Refractory Rheumatoid Arthritis Patients" Published Mar. 3, 2013. Retrieved from : https://clinicaltrials.gov/ct2/history/NCT01663116?A=4&B=4&C=merge#StudyPageTop (Year: 2013).*
International Search Report for International WIPO Application PCT/EP2016/059196 filed on Apr. 25, 2016.
"e-Newsletter ESGCT and SETGyC Collaborative Congress Consmtium Pmticipation". Document retrieved from internet. Published on Oct. 25, 2013. http://www.regenerar.eu/sites/default/files/REGENERAR_newsletter%202014%20-ESCGT.pdf.
De la Rosa et al., "Mesenchymal stem cells as therapeutic agents of inflammatory and autoimmune deseases," Curr. Op. Biotech. 2012, 23(6):978-983.
Ciccocioppo R. et al., "Autologous bone marrow-derived mesenchymal stromal cells in the treatment of fistulising Crohn's disease", Gut, 2011, vol. 60, No. 6, pp. 788-798.
"Conditioning Protocols-allogeneic transplantation", Clinical & Investigative Sciences Group et al. 2012, retrieved from Internet.
Dandan et al., Arthritis & Rheumatism, 2013, 65: S674-S675.
De la Rosa et al., "Requirement of IFN-γ-Mediated Indoleamine 2,3-Dioxygenase Expression in the Modulation of Lymphocyte Proliferation by Human Adipose-Derived Stem Cells", Tissue Engin., 2009, 15: 2795-2806.
Duijvestein M. et al., "Autologous bone marrow-derived mesenchymal stromal cell treatment for refractory luminal Crohn's disease: results of a phase I study", Gut, Oct. 4, 2010, vol. 59, No. 12, pp. 1662-1669.
Garcia-Olmo D. et al., "A Phase I Clinical Trial of the Treatment of Crohn's Fistula by Adipose Mesenchymal Stem Cell Transplantation", Dis Colon Rectum, 2005, vol. 48, No. 7, pp. 1416-1423.
Krampera M. et al., "Role for Interferon-γ in the Immunomodulatory Activity of Human Bone Marrow Mesenchymal Stem Cells", Stem Cells, 2006, 24: 386-398.
Krampera M, "Mesenchmal stromal cell 'licensing': a multistep process", Leukemia, 2011, 25: 1408-1414.
Liu Y. et al., "Mesenchymal Stem Cell-Based Tissue Regeneration is Governed by Recipient T Lymphocyte via IFN-γ and TNF-α", Nat Med., 2011, vol. 17, No. 12, pp. 1594-1601.

* cited by examiner

*Primary Examiner* — Allison M Fox
(74) *Attorney, Agent, or Firm* — Thomas | Horstemeyer, LLP

(57) ABSTRACT

The invention relates to a method for predicting the clinical response to a therapy based on the administration of mesenchymal stem cells (MSCs) in a patient suffering from an immune-mediated inflammatory disease. The invention also relates to methods of personalised medicine as well as to therapeutic uses of MSCs in a patient suffering from an immune-mediated inflammatory disease.

17 Claims, 7 Drawing Sheets

A

B

BIOMARKERS FOR DETERMINING THE CLINICAL RESPONSE TO CELL THERAPY

CROSS-REFERENCE TO RELATED APPLICATIONS

This application is the 35 U.S.C. § 371 national stage application of PCT Application No. PCT/EP2016/059196, filed Apr. 25, 2016, which claims priority to and the benefit of European Patent Application EP15382206.9 titled "BIOMARKERS FOR DETERMINING THE CLINICAL RESPONSE TO CELL THERAPY" filed Apr. 24, 1015, the entire disclosures of which are incorporated herein by reference.

FIELD OF THE INVENTION

The invention relates to the field of the use of biomarkers for predicting a clinical response to cell therapy, and more specifically to the use of biomarkers for predicting a clinical response to cell therapy in patients suffering from an immune-mediated inflammatory disease.

BACKGROUND OF THE INVENTION

Adult mesenchymal stem cells (MSCs) have been found in a variety of adult tissues. Having been first identified in the bone marrow, MSCs are now accepted to reside in other tissues of mesodermal origin: adipose tissue, placenta, umbilical cord, dental pulp, synovium. Despite ample efforts, no exclusive individual surface markers have been identified for MSCs. MSCs are defined according to the three criteria of the International Society for Cellular Therapy: a) Adhesion to plastic: MSCs can be isolated by adhesion to plastic and expanded in vitro in serum containing media with no additional requirements for growth factors or cytokines; b) Expression of a specific combination of surface markers: MSCs are negative for hematopoietic and endothelial markers such as CD11b, CD14, CD31, CD34 and CD45, and positive for a variety of other markers, including HLA class I, CD73, CD90 and CD105; c) Differentiation potential: MSCs can be identified in vitro by their ability to differentiate into mesenchymal-type cells (e.g. trilineage differentiation into adipocytes, osteoblasts and chondrocytes). MSCs are at least tripotent at early stages which may be reduced to e.g. bipotent or unipotent cells in the course of in vitro expansion processes. Although sharing these main characteristics, differences between MSCs from different sources can be found. Accordingly, the secretome differs between cell types, and bone marrow-derived MSCs (BM-MSCs) and adipose-derived MSCs (ASCs) show specific RNA and protein expression profiles.

MSCs are considered a promising tool for cell therapy in regenerative medicine, or for treating other diseases such as ischemic, inflammatory and immune diseases. Although in situ differentiation was initially thought to be the basis of their therapeutic properties (i.e. structural tissue regeneration), it is now believed that their immunomodulatory capacity and paracrine effects through trophic factors with anti-fibrotic, anti-apoptotic or pro-angiogenic properties are the more likely mechanisms of their therapeutic effect.

MSCs show immunomodulation properties and regulate the function (proliferation, activation and effector function) of a broad variety of immune cells including B lymphocytes, T lymphocytes, NK cells, monocyte-derived dendritic cells and neutrophils. The specific molecular and cellular mechanisms involved in the immunoregulatory activity of MSCs are still under investigation but rely on both cell contact-dependent mechanisms (i.e. through Jagged1-Notch1 interaction) and paracrine effects through the release of soluble factors including hepatocyte growth factor (HGF), prostaglandin-E2 (PGE2), transforming growth factor (TGF)-beta 1, indoleamine 2,3-dioxygenase (IDO), nitric oxide (NO), interleukin (IL)-10, IL-6, heme oxygenase-1 (HO-1) or HLA-G5. Furthermore, MSCs may also modulate immune responses through the generation of Regulatory T cells ($T_{regs}$). These cells are defined by the expression of CD4, CD25 and the transcription factor Forkhead box p3 (Foxp3), and play a central role in protecting from autoimmunity through their immunosuppressive capacity.

In addition to this immunomodulatory capacity, an additional potential advantage of the clinical use of MSC is that the immunogenicity of MSC is considered to be low. This is due to the fact that the expression of HLA class I is low, and HLA class II and the classic co-stimulatory molecules CD40, CD80 and CD86 are not detectable.

One of the first reported (1995) clinical trials involving MSC was the bone marrow derived stromal progenitor cell therapy in the treatment of patients having hematologic malignancies. Since then numerous clinical trials have been carried out and the first marketing authorizations have been granted for MSC therapies. Currently there are several hundred trials reported involving MSC, for the treatment of indications including bone disorders (e.g. bone cysts, cleft palate, osteonecrosis, spinal fusion), cartilage disorders (e.g. articular cartilage repair and meniscus repair), hematologic disorders (e.g. anaemia, myelodysplastic syndrome), metabolic diseases (e.g. Type I & II diabetes), liver diseases (e.g. cirrhosis & failure), cardiovascular diseases (e.g. AMI), gastrointestinal disorders (e.g. IBD and anal fistula), autoimmune disorders (e.g. rheumatoid arthritis and Crohn's disease), pulmonary diseases (e.g. COPD and IPF), neurological diseases (e.g. MS, stroke and disc degeneration), renal diseases (e.g. kidney failure and renal transplant), urogenital disorders (e.g. urinary incontinence & erectile dysfunction) and ophthalmological diseases (e.g. retinitis pigmentosa).

While such on-going investigations illustrate the potential of MSCs in treating a wide variety of diseases and disorders the use of biomarkers for the prediction of treatment response may potentially aid in the development and use of such therapies.

SUMMARY OF THE INVENTION

The authors of the present invention have identified several biomarkers that can predict response to cell therapy in patients suffering from an immune-mediated inflammatory disease when measured prior to treatment. In particular, the level of monocytes, and/or the level of $T_{reg}$ cells, and/or the ratio of CD4$^+$ T cells to $T_{reg}$ cells (CD4$^+$/$T_{reg}$), and/or the level of T cell proliferation capacity are able to discriminate between responders and the rest of the population, which are non-responders.

Thus, in a first aspect, the invention relates to a method for predicting the clinical response to a therapy based on the administration of mesenchymal stem cells (MSCs) in a patient suffering from an immune-mediated inflammatory disease, comprising determining in a sample from the patient a parameter selected from the group consisting of:
 i) the level of monocytes,
 ii) the level of $T_{reg}$ cells
 iii) the ratio of CD4+ T cells to $T_{reg}$ cells (CD4+/$T_{reg}$),
 iv) the T cell proliferation capacity, wherein
an increased level of monocytes in said sample with respect to a reference value is indicative of a clinical response to said therapy based on the administration of MSCs,
a decreased level of $T_{reg}$ cells with respect to a reference value is indicative of a clinical response to said therapy based on the administration of MSCs,
an increased ratio of CD4+ T cells to $T_{reg}$ cells (CD4+/$T_{reg}$) with respect to a reference value is indicative of a clinical response to said therapy based on the administration of MSCs,
an increased T cell proliferation capacity with respect to a reference value is indicative of a clinical response to said therapy based on the administration of MSCs.

In a second aspect, the invention relates to a method for selecting a patient suffering from an immune-mediated inflammatory disease to receive a therapy based on the administration of MSCs, comprising determining in a sample from the patient a parameter selected from the group consisting of:
  i) the level of monocytes,
  ii) the level of $T_{reg}$ cells
  iii) the ratio of CD4+ T cells to $T_{reg}$ cells (CD4+/$T_{reg}$),
  iv) the T cell proliferation capacity,
wherein
an increased level of monocytes in said sample with respect to a reference value is indicative of a clinical response to said therapy based on the administration of MSCs,
a decreased level of $T_{reg}$ cells with respect to a reference value is indicative of a clinical response to said therapy based on the administration of MSCs,
an increased ratio of CD4+ T cells to $T_{reg}$ cells (CD4+/$T_{reg}$) with respect to a reference value is indicative of a clinical response to said therapy based on the administration of MSCs,
an increased T cell proliferation capacity with respect to a reference value is indicative of a clinical response to said therapy based on the administration of MSCs.

In a third aspect, the invention relates to a method for selecting a therapy for treating a patient suffering from an immune-mediated inflammatory disease, comprising determining in a sample from the patient a parameter selected from the group consisting of:
  i) the level of monocytes,
  ii) the level of $T_{reg}$ cells,
  iii) the ratio of CD4+ T cells to $T_{reg}$ cells (CD4+/$T_{reg}$),
  iv) the T cell proliferation capacity,
wherein
an increased level of monocytes in said sample with respect to a reference value is indicative of a clinical response to said therapy based on the administration of MSCs,
a decreased level of $T_{reg}$ cells with respect to a reference value is indicative of a clinical response to said therapy based on the administration of MSCs,
an increased ratio of CD4+ T cells to $T_{reg}$ cells (CD4+/$T_{reg}$) with respect to a reference value is indicative of a clinical response to said therapy based on the administration of MSCs,
an increased T cell proliferation capacity with respect to a reference value is indicative of a clinical response to said therapy based on the administration of MSCs.

In another aspect, the invention relates to the use of a kit comprising reagents suitable for determining a parameter selected from the group consisting of:
  i) the level of monocytes,
  ii) the level of Treg cells,
  iii) the ratio of CD4+ T cells to Treg cells (CD4+/Treg),
  iv) the T cell proliferation capacity,
for predicting the clinical response to a therapy based on the administration of MSCs in a patient suffering from an immune-mediated inflammatory disease and/or for selecting a patient suffering from an immune-mediated inflammatory disease to receive a therapy based on the administration of MSCs and/or for selecting a therapy for treating a patient suffering from an immune-mediated inflammatory disease.

In another aspect, the invention relates to MSCs for use in the treatment of an immune-mediated inflammatory disease in a patient in need thereof, wherein the patient has
an increased level of monocytes with respect to a reference value,
a decreased level of $T_{reg}$ cells with respect to a reference value,
an increased CD4+/$T_{reg}$ ratio with respect to a reference value,
an increased T cell proliferation capacity with respect to a reference value,

DETAILED DESCRIPTION OF THE INVENTION

Definitions

Figure 1:
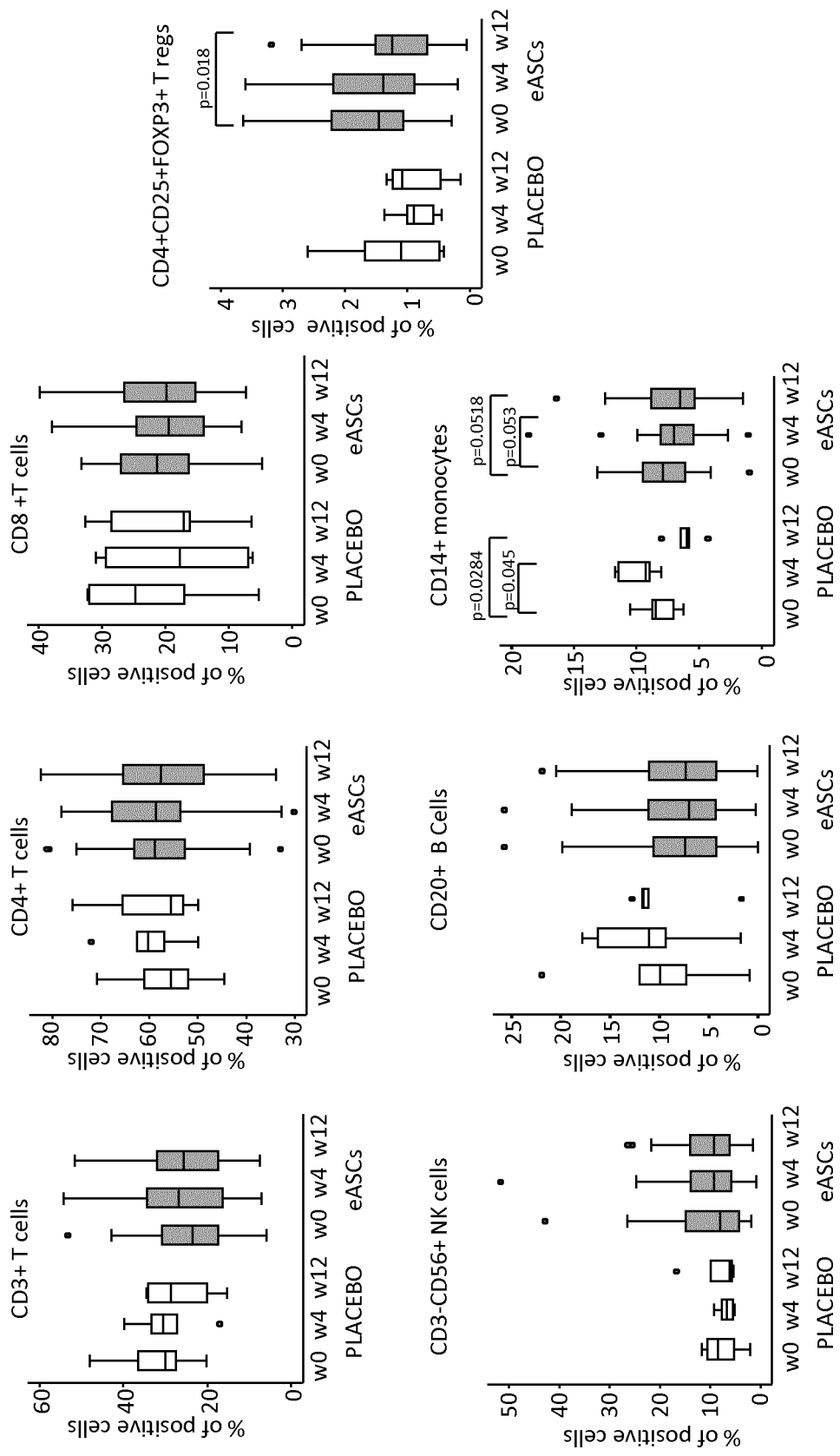
FIG. 1.—Cell populations in peripheral blood in eASC treated and placebo groups.—Percentage of positive cells at baseline (week 0), week 4 and week 12 after ASC or placebo administration is shown. T cells (CD3/CD4/CD8), NK Cells (CD56+), B cells (CD20+), monocytes (CD14+) and $T_{reg}$ cells (CD4+CD25+FoxP3+) were analysed. All data are presented as the interquartile range (p75 upper edge, p25 lower edge, p50 midline), p95 (line above the box), and p5 (line below the box) of the different immunological parameters. Dots represent the outliers. Significance was analysed by the Mann-Whitney test.

In order to facilitate the understanding of the present description, the meaning of some terms and expressions in the context of the invention will be explained below. Further definitions will be included throughout the description as necessary.

The terms "mesenchymal stem cell", "immune cell" and "fibroblast cell" shall be taken to encompass the progeny thereof, including but not limited to ex vivo cultured descendants thereof. It will be understood that progeny cells may be obtained after any number of passages from the parental population. However, in certain embodiments, the progeny cells may be obtained after about 2, about 3, about 4, about 5, about 6, about 7, about 8, about 9, or about 10 passages from the parental population.

The term "mesenchymal stem cell" or "MSC" or "mesenchymal stromal stem cell", as used herein, are multipotent stem cells, i.e. they are cells which are capable of giving rise to multiple different types of cells. The term refers to cells which are capable of differentiating into at least one of an osteoblast, a chondrocyte, an adipocyte, or a myocyte. MSCs may be isolated from any type of tissue. Generally MSCs will be isolated from bone marrow, adipose tissue, umbilical cord, or peripheral blood. The MSCs used in the invention may in some embodiments be isolated from bone marrow (BM-MSCs) or adipose tissue (ASCs). In a preferred aspect of the invention, MSCs are obtained from lipoaspirates, themselves obtained from adipose tissue. The term as used herein shall be taken to include the progeny of said MSC, for example but not limited to subcultured descendants thereof.

The MSCs used in the present invention are preferably characterised in that (i) they do not express markers specific for antigen presenting cells, (ii) they do not express IDO (Indoleamine 2,3-Dioxygenase) constitutively, (iii) they express IDO upon stimulation with IFN-gamma, and (iv) they present the capacity to be differentiated into at least two cell lineages. Alternatively, the MSCs used in the present invention are preferably characterised by the presence and absence of a set of markers, namely, said cells are characterised in that (i) they express CD9, CD10, CD13, CD29, CD44, CD49a, CD51, CD54, CD55, CD58, CD59, CD90 or CD105, and (ii) they do not express CD11b, CD14, CD15, CD16, CD31, CD34, CD45, CD49f, CD102, CD104, CD106 or CD133.

By "adipose tissue", it is meant any fat tissue. The adipose tissue may be brown or white adipose tissue, derived from, for example, subcutaneous, omental/visceral, mammary, gonadal, periorgan or other adipose tissue site. Preferably, the adipose tissue is subcutaneous white adipose tissue. The adipose tissue may comprise a primary cell culture or an immortalized cell line. The adipose tissue may be from any organism having fat tissue. In some embodiments, the adipose tissue is mammalian, and in further embodiments the adipose tissue is human. A convenient source of adipose tissue is liposuction surgery. However, it will be understood that neither the source of adipose tissue nor the method of isolation of adipose tissue is critical to the invention. If cells as described herein are desired for autologous transplantation into a subject, the adipose tissue will be isolated from that subject.

"Adipose tissue-derived stromal stem cells" or "ASCs" or "ADSCs", as used herein, refers to MSCs that originate from adipose tissue, generally from human adipose tissue (hASCs).

The term "stromal cell", as used herein, refers to a connective tissue cell of any organ. Fibroblasts and pericytes are among the most common types of stromal cells.

The term "immune cell", as used herein, refers to a cell of the immune system, which originates in the bone, matures and migrates to guard the peripheral tissues, circulating in blood and lymph vessels. Immune cells originate from a pluripotent haematopoietic stem cell, which gives rise to lymphoid lineages responsible for adaptive immunity, and also to myeloid lineages that participate in both innate and adaptive immunity. The lymphoid lineages includes cells that differentiate into natural killer cells (NK cells), T cells and B cells, and the myeloid lineages include cells that differentiate into monocytes and macrophages, dendritic cells, neutrophils, basophils, and eosinophils.

The term "natural killer cell" or "NK cell", as used herein, refers to a type of cytotoxic lymphocyte that provides rapid responses to viral-infected cells and responds to tumour formation. NK cells are characterised for expressing CD16 and CD56.

The term "T lymphocyte" or "T cell", as used herein, refers to a type of lymphocyte characterised by expressing a T-cell receptor (TCR) on the cell surface, which plays a central role in cell-mediated immunity. There are several types of T cells, including helper T cells (CD4+), cytotoxic T cells (CD8+), memory T cells (CD45RO), regulatory T cells ($T_{regs}$) (CD4+CD25brightFoxp3+ or induced CD4+ CD25bright cells), and natural killer T cells (NKT cells). Upon activation of the T cells, they begin expressing the so-called "early and/or intermediate activation markers". "Early and/or intermediate T cell-activation markers" include CD69, HLA-DR, CD25, CD71, CD154, CD38, and CD27.

The term "B lymphocyte" or "B cell", as used herein, refers to a lymphocyte that plays a role in humoral immunity of the adaptive immune system, and which is characterised by the presence of the B cell receptor (BCR) on the cell surface. B cell types include plasma cells, memory B cells, B-1 cells, B-2 cells, marginal-zone B cells, follicular B cells, and regulatory B cells ($B_{reg}$).

The term "monocyte", as used herein, refers to an immune cell that circulates in the blood for about one to three days and then migrates from the bloodstream to other tissues where it will then differentiate into tissue resident macrophages or dendritic cells.

The term "macrophage", as used herein, refers to a cell produced by the differentiation of monocytes. Macrophages are characterised by the expression of CD14, CD40, CD11b, CD64, EMR1, lysozyme M, MAC-1/MAC-3 and CD68.

The term "dendritic cell", as used herein, refers to an antigen presenting cell present in those tissues that are in contact with the external environment. Dendritic cells enter the tissues as immature phagocytes where they specialise in ingesting antigens.

Neutrophils, eosinophils, and basophils are collectively known as granulocytes; they circulate in the blood unless recruited to act as effector cells at sites of infection and inflammation. Mast cells are exocytic and are thought to orchestrate the defence against parasites as well as triggering allergic inflammation; they recruit eosinophils and basophils, which are also exocytic.

The term "neutrophil", as used herein, refers to a type of granulocyte characterised by CD68 and CD15 expression.

The term "basophil", as used herein, refers to a type of granulocyte characterised by the following marker pattern: FcεRI+, CD123, CD49b(DX-5)+, CD69+, Thy-1.2+, 2B4+, CD11bdull, CD117(c-kit)−, CD24−, CD19−, CD80−, CD14−, CD23−, Ly49c−, CD122−, CD11c−, Gr-1−, NK1.1−, B220−, CD3−, γδTCR−, αβTCR−, α4 and β4-integrin negative. Basophils appear in many specific kinds of inflammatory reactions, particularly those that cause allergic symptoms.

The term "eosinophil", as used herein, refers to a type of granulocyte characterised by Siglec-F expression.

The term "fibroblast cell" as used herein refers to mesenchyme derived connective tissue cells that are associated with the synthesis and maintenance of extra cellular matrix and shall be taken to include fibroblast like synovial cells.

The term "allogeneic" as used herein shall be taken to mean from different individuals of the same species. Two or more individuals are said to be allogeneic to one another when the genes at one or more loci are not identical.

The term "autologous" as used herein shall be taken to mean from the same individual.

The term "expanded cells", as used herein, refers to cells that are cultured ex vivo.

The term "patient" as used herein refers to all animals classified as mammals and includes, without limitation, domestic and farm animals, primates and humans, e.g., human beings, non-human primates, cows, horses, pigs, sheep, goats, dogs, cats, or rodents suffering from a disorder or disease. Preferably, the patient is a male or female human of any age or race.

The term "immune-mediated inflammatory disease" or "IMID", as used herein, refers to any of a group of conditions or diseases that lack a definitive etiology, but which are characterised by common inflammatory pathways leading to inflammation, and which may result from, or be triggered by, a dysregulation of the normal immune response. Because inflammation mediates and is the primary driver of many medical and autoimmune disorders, within the context of the present invention, the term immune-mediated inflammatory disease is also meant to encompass autoimmune disorders and inflammatory diseases.

The term "autoimmune disorder" refers to a condition in a subject characterised by cellular, tissue and/or organ injury, caused by an immunological reaction of the subject to its own cells, tissues and/or organs. Illustrative, non-limiting examples of autoimmune diseases which can be treated with the methods or pharmaceutical compositions of the invention include alopecia areata, rheumatoid arthritis (RA), ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, anti-glomerular gasement membrane disease, antiphospholipid syndrome, autoimmune diseases of the nervous system, familial mediterranean fever, Lambert-Eaton myasthenic syndrome, sympathetic ophthalmia, polyendocrinopathies, psoriasis, etc.

The term "inflammatory disease" refers to a condition in a subject characterised by inflammation, e.g. chronic inflammation. Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, chronic inflammation resulting from chronic viral or bacterial infections, and acute inflammation, such as sepsis.

The term "refractory", as used herein, refers to a disorder or disease that does not respond or becomes resistant to the established therapeutic treatment.

The term "treat" or "treatment" or "treating", as used herein, when used directly in reference to a patient or subject shall be taken to mean the administration of a therapy to a patient subject in need of said treatment for the amelioration of one or more symptoms associated with a disease or disorder. Those in need of treatment include those already with the condition or disorder as well as those prone to have the condition or disorder or those in which the condition or disorder is to be prevented. The terms "treat" or "treatment" or "treating" when used directly in reference to damaged tissues shall be taken to mean the amelioration of such damage by both direct mechanisms such as the regeneration of damaged tissues, repair or replacement of damaged tissues (e.g. by scar tissue) as well as through indirect mechanisms e.g., reducing inflammation thereby enabling tissue formation.

The terms "clinical responsiveness" or "clinical response" or "treatment response", as used herein, shall be taken to mean change of one or more clinical signs associated with a disease or disorder, wherein said change results from the administration of a pharmaceutical composition to a subject in need of said treatment or therapy.

The term "predicting the clinical response", is used herein to refer to the likelihood that a patient will have a particular clinical outcome, whether positive or negative. The predictive methods of the present invention can be used clinically to make treatment decisions by choosing the most appropriate treatment modalities for any particular patient. The predictive methods of the present invention are valuable tools in predicting if a patient is likely to respond favourably to a treatment regimen, such as cell therapy. The prediction may also include prognostic factors. As it will be understood by those skilled in the art, the prediction, although preferred to be, need not be correct for 100% of the patients to be evaluated. The term, however, requires that a statistically significant portion of subjects can be identified as having an increased probability of having a given clinical response.

The term "determining", as used herein, relates to the determination of any parameter that can be useful in predicting the clinical response of a patient. As will be understood by those skilled in the art, the determination of a parameter, although preferred to be, need not be correct for 100% of the subjects to be diagnosed or evaluated. The term, however, requires that a statistically significant portion of subjects can be identified as presenting a given parameter.

Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

The term "responder" shall be taken to mean a patient having an immune-mediated inflammatory disease wherein a treatment ameliorates or improves or prevents worsening of one or more symptoms thereof or otherwise provides therapeutic benefit wherein said change results from said treatment. In contrast, the term "non-responder" or a patient classified as "rest of population" shall be taken to mean a patient having an immune-mediated inflammatory disease wherein a treatment does not ameliorate or improve one or more symptoms thereof or does not provide therapeutic benefit to the patient.

The term "culture", as used herein, refers to the growth of cells, organisms, multicellular entities, or tissue in a medium. The term "culturing" refers to any method of achieving such growth, and may comprise multiple steps.

The term "culture medium" or "medium" is recognised in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to.

The terms "comprise" and "comprising" are used in the inclusive, open sense, meaning that additional elements may be included.

The term "including" is used herein to mean "including but not limited to" or "including without limitation". These terms are used interchangeably.

1. Predictive Method

The inventors have shown that the levels of several biomarkers in patients suffering from an immune-mediated inflammatory disease before treatment can be used to prospectively distinguish those patients who will respond to cell therapy, i.e. the responders, from those patients who will not, i.e. the non-responders.

Thus, in a first aspect, the invention relates to a method for predicting the clinical response to a therapy based on the administration of mesenchymal stem cells (MSCs) in a patient suffering from an immune-mediated inflammatory disease, hereinafter "the predictive method of the invention", comprising determining the level of monocytes, and/or the level of $T_{reg}$ cells, and/or the ratio of CD4+ T cells to $T_{reg}$ cells (CD4+/$T_{reg}$), and/or the T cell proliferation capacity in a blood sample obtained from said patient, wherein an increased level of monocytes in respect to a reference value, and/or a decreased level of $T_{reg}$ cells in respect to a reference value, and/or an increased ratio of CD4$^+$ T cells to $T_{reg}$ cells (CD4$^+$/$T_{reg}$) in respect to a reference value, and/or an increased T cell proliferation capacity is indicative of a clinical response to said therapy based on the administration of MSCs.

The predictive method of the invention comprises a step of determining the level of monocytes, and/or the level of $T_{reg}$ cells, and/or the ratio of CD4+ T cells to $T_{reg}$ cells (CD4+/$T_{reg}$), and/or the T cell proliferation capacity in a blood sample obtained from said patient.

Methods for the measurement of monocytes, $T_{reg}$ cells and CD4$^+$ T cells populations are well known in the art. The gold standard method for quantification of said cells is flow cytometry. Staining panels are commercially available for the fluorescence tag detection of said cell populations. Typically % of each subpopulation is determined by staining for the specific marker for each cell population. Conversion of % to cell counts can be carried out by using a volumetric approach, either by analysing a fixed volume of sample or by recording the volume of any given sample. Optionally, specific cell surface markers, such as CD4 may be detected using conventional methods and apparatus (for example a Becton Dickinson FACSCalibur system used with commercially available antibodies and standard protocols known in the art). Alternatively beads-based systems allow the conversion of % to absolute cell counts by using fluorescent beads to spike samples and thus measure sample volume. The volumetric or beads-based approaches are referred to as single platform approaches, and are commercially available e.g. TruCount (Becton Dickinson) and FlowCould (Beckman Coulter). Additionally, dedicated platforms for CD4$^+$ analysis are also available e.g. FACScount (Becton Dickinson). An alternative methodology for cell quantification is the use of a haematology analyser for measurement of total lymphocyte count as a reference for the FACS measurement. Often referred to as the "dual platform" approach, approaches such as "pan-leucogating" are known in the art for the quantification of lymphocyte sub-populations using the combined platform approach. As an alternative to flow cytometry manual methods using microscopy in combination with haemocytometers are known. Commercially available kits utilise immunomagnetic beads for the isolation of cell subpopulations that may be subsequently counted under the microscope. Any other standard technique for determining the levels of cells in blood samples may also be used, such as ELISA.

Prior to determining the levels of cells, the blood sample may be processed in order to purify, isolate or concentrate the present cells by means of any conventional technique.

In a particular embodiment, the predictive method of the invention comprises a step of determining the level of monocytes. In another particular embodiment, the predictive method of the invention comprises a step of determining the level of $T_{reg}$ cells. In another particular embodiment, the predictive method of the invention comprises a step of determining the ratio of CD4+ T cells to $T_{reg}$ cells (CD4+/$T_{reg}$) in a blood sample obtained from said patient. In another particular embodiment, the predictive method of the invention comprises a step of determining the T cell proliferation capacity in a blood sample obtained from said patient.

In another particular embodiment, the predictive method of the invention comprises a step of determining the levels of monocytes and $T_{reg}$ cells in a blood sample obtained from said patient. In another particular embodiment, the predictive method of the invention comprises a step of determining the levels of monocytes and the ratio of CD4+ T cells to $T_{reg}$ cells (CD4+/$T_{reg}$) in a blood sample obtained from said patient. In another particular embodiment, the predictive method of the invention comprises a step of determining the levels of $T_{reg}$ cells and the ratio of CD4+ T cells to $T_{reg}$ cells (CD4+/$T_{reg}$) cells in a blood sample obtained from said patient. In another particular embodiment, the predictive method of the invention comprises a step of determining the levels of monocytes and the T cell proliferation capacity in a blood sample obtained from said patient. In another particular embodiment, the predictive method of the invention comprises a step of determining the levels of $T_{reg}$ cells and the T cell proliferation capacity in a blood sample obtained from said patient. In another particular embodiment, the predictive method of the invention comprises a step of determining the ratio of CD4+ T cells to $T_{reg}$ cells (CD4+/$T_{reg}$) and the T cell proliferation capacity in a blood sample obtained from said patient.

In another particular embodiment, the predictive method of the invention comprises a step of determining the levels of monocytes, $T_{reg}$ cells and the ratio of CD4+ T cells to $T_{reg}$ cells (CD4+/$T_{reg}$) in a blood sample obtained from said patient. In another particular embodiment, the predictive method of the invention comprises a step of determining the levels of monocytes and $T_{reg}$ cells and the T cell proliferation capacity in a blood sample obtained from said patient. In another particular embodiment, the predictive method of the invention comprises a step of determining the levels of monocytes the ratio of CD4+ T cells to $T_{reg}$ cells (CD4+/$T_{reg}$) and the T cell proliferation capacity in a blood sample obtained from said patient. In another particular embodiment, the predictive method of the invention comprises a step of determining the levels of $T_{reg}$ cells and the ratio of CD4+ T cells to $T_{reg}$ cells (CD4+/$T_{reg}$) and the T cell proliferation capacity in a blood sample obtained from said patient.

In another particular embodiment, the predictive method of the invention comprises a step of determining the levels of monocytes, $T_{reg}$ cells and the ratio of CD4+ T cells to $T_{reg}$ cells (CD4+/$T_{reg}$) and the T cell proliferation capacity in a blood sample obtained from said patient.

According to the predictive method of the invention, an increased level of monocytes in respect to a reference value, and/or a decreased level of $T_{reg}$ cells in respect to a reference value, and/or an increased ratio CD4$^+$/$T_{reg}$ in respect to a reference value, and/or an increased T cell proliferation capacity in respect to a reference value is indicative of a clinical response to said therapy based on the administration of MSCs, immune cells, fibroblasts or combinations thereof.

As used herein, the term "T cell proliferation" refers to the number of T-cells produced during the incubation of T-cells with the antigen presenting cells, with or without the presence of antigen. The T cell proliferation capacity of T cells in an individium can be determined using methods well-known in the art, such as by measuring the capacity of the a T cell population to incorporate labelled nucleotides into their DNA (e.g. triatiated thymidine or 5-bromo-2'-deoxyuridine), by measuring appearance of the activation marker CD38 (e.g. by FACS), by measuring the decrease in the fluorescence intensity of T cells labelled with 5,6-carboxyfluorescein diacetate succinimidyl ester (CFSE).

The term "reference value", as used herein, relates to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. The reference value according to the predictive method of the invention is obtained from the values of the level of monocytes, and/or the level of $T_{reg}$ cells, and/or the ratio $CD4^+/T_{reg}$, and/or the T cell activation capacity in a blood sample obtained from one or more patients who do not respond to a therapy based on the administration of MSCs, i.e. from one or more non-responding patients or "non-responders".

In the context of the invention, the level of a certain cell type is considered to be "increased" when the level of said cell type in a sample is higher than a reference value. The level of a cell type is considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or higher than its reference value.

Likewise, the level of a certain cell type is considered to be "decreased" when the level of said cell type in a sample is lower than a reference value. The level of a cell type is considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or lower than its reference value.

In a particular embodiment, the MSCs on which the therapy is based are allogeneic. In another particular embodiment, the MSCs on which the therapy is based are autologous.

In another particular embodiment, the therapy is based on the administration of MSCs. In a preferred embodiment, the MSCs are adipose tissue-derived stem cells or adipose tissue-derived stromal cells (ASCs).

In another particular embodiment, the MSCs are expanded MSCs, immune cells, fibroblasts or combinations thereof. The term "expanded cells", as used herein, refers to cells which are maintained and allowed to proliferate ex vivo upon isolation. Methods for the ex vivo expansion of MSC populations are known in the art. Taking MSCs as an example, subsequent to isolation MSC can be maintained and allowed to proliferate ex vivo in a cell culture medium. Such medium may be composed of, for example, Dulbecco's Modified Eagle's Medium (DMEM), with antibiotics (for example, 100 units/ml Penicillin and 100 μg/ml Streptomycin) or without antibiotics, and 2 mM glutamine, and supplemented with 2%-20% foetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include foetal bovine serum (FBS), bovine serum (BS), calf serum (CS), foetal calf serum (FCS), newborn calf serum (NCS), goat serum (GS), horse serum (HS), porcine serum, sheep serum, rabbit serum, rat serum (RS), etc. It is also within the scope of the invention that if said MSC are of human origin, the cell culture medium is supplemented with a human serum, preferably of autologous origin. It is understood that sera can be heat-inactivated at 55-65° C. if deemed necessary to inactivate components of the complement cascade. Modulation of serum concentrations and/or withdrawal of serum from the culture medium can also be used to promote survival of one or more desired cell types. Preferably, said MSC will benefit from FBS concentrations of about 2% to about 25%. In another embodiment, the MSC can be expanded in a cell culture medium of definite composition, in which the serum is replaced by a combination of serum albumin, serum transferrin, selenium, and recombinant proteins including but not limited to insulin, platelet-derived growth factor (PDGF), and basic fibroblast growth factor (bFGF) as known in the art.

In a preferred embodiment the cells may be cultured for at least about 15 days, at least about 20 days, at least about 25 days, or at least about 30 days. The expansion of cells in culture may improve the homogeneity of the cell phenotype in the cell population, accordingly in a preferred embodiment said cells are cultured until substantially homogenous. More preferably, the cells are expanded in culture for at least three culture passages or "passaged at least three times". In other preferred embodiments, the cells are passaged at least four times, at least five times, at least six times, at least seven times, at least eight times, at least nine times, or at least ten times. It is appreciated that multilineage differentiation potential of the cells may decrease during expansion, e.g. with successive passaging of the cells; such progeny cells are nonetheless within the scope of the embodiments of the present invention. Methods for cell expansion are known in the art and may comprise the use of commercially available 2D or 3D bioreactors.

In another particular embodiment, the MSCs are administered systemically, preferably via the rectal, nasal, buccal, vaginal, subcutaneous, intracutaneous, intravenous, intraperitoneal, intramuscular, intraarticular, intrasynovial, intrasternal, intrathecal, intralesional, or intracranial route, or via an implanted reservoir. In another particular embodiment, the MSCs are administered locally.

In another particular embodiment, the immune-mediated inflammatory disease is an autoimmune disorder.

In another particular embodiment, the immune-mediated inflammatory disease is an inflammatory disease selected from the group consisting of Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, and chronic inflammation resulting from chronic viral or bacterial infections, preferably RA.

In a more preferred embodiment, the RA is refractory.

In another preferred embodiment, the patient is refractory to at least one biological treatment. Non-limitative examples of biological therapeutics indicated for RA include tumour necrosis factor alpha (TNFα) inhibitors, such as infliximab, Adalimumab (Humira), Certolizumab (Cimzia), Etanercept (Enbrel), and Golimumab (Simponi); interleukin 1 (IL-1) inhibitors, such as anakinra, interleukin 6 (IL-6) inhibitors, such as tocilizumab, T cell costimulation inhibitors, such as abatacept, and anti-CD20 antibodies, such as rituximab (Rituxan). In a more preferred embodiment, the patient is refractory to at least a TNFα inhibitor selected from the group consisting of Adalimumab (Humira), Certolizumab (Cimzia), Etanercept (Enbrel), Golimumab (Simponi), and Infliximab (Remicade). In another more preferred embodiment, the patient is refractory to at least an IL-1 inhibitor, such as anakinra. In another more preferred embodiment, the patient is refractory to at least an IL-6 inhibitor, such as tocilizumab. In another more preferred embodiment, the patient is refractory to at least a T cell costimulation inhibitor, such as abatacept. In another more preferred embodiment, the patient is refractory to at least an anti-CD20 antibody, such as rituximab (Rituxan).

In another particular embodiment, the predictive method of the invention requires that the parameter in the patient is determined prior to the administration of the therapy based on the administration of MSCs, whereby an increased T cell proliferation capacity, a decreased level of $T_{reg}$ cells, an increased ratio of CD4+ T cells to $T_{reg}$ cells (CD4+/$T_{reg}$) and/or an increased level of monocytes are indicative that the patient shows a high probability of showing a positive response to the administration of the MSCs.

2. Methods of Personalised Medicine

According to the previous aspects of the invention, the determination of a series of biomarkers allows the identification of patients with an immune-mediated inflammatory disease who are susceptible of having a clinical response to cell therapy. Therefore, this information can be used for the identification of patients which would benefit from the treatment with such therapy.

2.1. Methods for Selecting Patients to Receive a Therapy

Thus, in another aspect, the invention relates to a method for selecting a patient suffering from an immune-mediated inflammatory disease to receive a therapy based on the administration of MSCs, hereinafter "the first method of personalised medicine of the invention", comprising determining the level of monocytes, and/or the level of $T_{reg}$ cells, and/or the ratio of CD4+ T cells to $T_{reg}$ cells (CD4+/$T_{reg}$), and/or the T cell proliferation capacity in a blood sample obtained from said patient, wherein an increased level of monocytes in respect to a reference value, and/or a decreased level of $T_{reg}$ cells in respect to a reference value, and/or an increased ratio of CD4$^+$ T cells to $T_{reg}$ cells (CD4$^+$/$T_{reg}$) in respect to a reference value, and/or an increased T cell proliferation capacity in respect to a reference value selects said patient to receive said therapy based on the administration of MSCs.

The definitions and particular embodiments relating to the terms "therapy", "patient", "immune-mediated inflammatory disease", and "reference value" have been described in detail in the context of the predictive method of the invention and apply equally to the first method of personalised medicine of the invention.

In a particular embodiment, the first method of personalised medicine of the invention requires that the parameter which is used for selecting the patient is determined in the patient sample prior to the administration of the therapy based on the administration of MSCs, whereby an increased T cell proliferation capacity, a decreased level of $T_{reg}$ cells, an increased ratio of CD4+ T cells to $T_{reg}$ cells (CD4+/$T_{reg}$) and/or an increased level of monocytes are indicative that the patient shows a high probability of showing a positive response to the administration of the MSCs and, accordingly, that it is candidate for being selected for receiving a therapy based on the administration of MSCs.

It will be immediately understood by the person skilled in the art that the first method of personalised medicine of the invention have the steps of determining the levels of cell or biomarkers in samples taken from the patient in common with the first, second and third predictive methods of the invention. Accordingly, the particular and preferred embodiments of the determination steps of the predictive methods of the invention are equally applied here.

2.2. Methods for Selecting a Therapy for a Patient

In another aspect, the invention relates to a method for selecting a therapy for treating a patient suffering from an immune-mediated inflammatory disease, hereinafter "the second method of personalised medicine of the invention", comprising determining the level of monocytes, and/or the level of $T_{reg}$ cells, and/or the ratio of CD4+ T cells to $T_{reg}$ cells (CD4+/$T_{reg}$), and/or the T cell proliferation capacity in a blood sample obtained from said patient, wherein an increased level of monocytes in respect to a reference value, and/or a decreased level of $T_{reg}$ cells in respect to a reference value, and/or an increased ratio of CD4$^+$ T cells to $T_{reg}$ cells (CD4$^+$/$T_{reg}$) in respect to a reference value, and/or an increased T cell proliferation capacity in respect to a reference value, selects a therapy based on the administration of MSCs.

The definitions and particular embodiments relating to the terms "therapy", "patient", "immune-mediated inflammatory disease", and "reference value" have been described in detail in the context of the predictive method of the invention and apply equally to the first and second methods of personalised medicine of the invention of the invention.

It will be immediately understood by the person skilled in the art that the first and second methods of personalised medicine of the invention have the steps of determining the levels of cell or biomarkers in samples taken from the patient in common with the predictive method of the invention. Accordingly, the particular and preferred embodiments of the determination steps of the predictive method of the invention are equally applied here.

3. Uses of the Invention

The present invention also contemplates the uses of reagents in for the purposes of the predictive method and methods of personalised medicine of the invention.

Thus, in another aspect, the invention relates to the use of a kit, hereinafter, comprising reagents suitable for determining the level of monocytes, and/or the level of $T_{reg}$ cells, and/or the ratio of CD4+ T cells to $T_{reg}$ cells (CD4+/$T_{reg}$), and/or the T cell proliferation capacity, for predicting the clinical response to a therapy based on the administration of MSCs in a patient suffering from an immune-mediated inflammatory disease.

In a particular embodiment, said kit further comprises MSCs.

In another aspect, the invention relates to the use of a kit comprising reagents suitable for determining the level of monocytes and/or the level of $T_{reg}$ cells and/or the ratio of CD4+ T cells to $T_{reg}$ cells (CD4+/$T_{reg}$), and/or the T cell proliferation capacity, for selecting a patient suffering from an immune-mediated inflammatory disease to receive a therapy based on the administration of MSCs, and/or for selecting a therapy for treating a patient suffering from an immune-mediated inflammatory disease.

In a particular embodiment, said kit further comprises MSCs.

The definitions and particular embodiments relating to the terms "therapy", "patient" and "immune-mediated inflammatory disease" have been described in detail in the context of the predictive method of the invention and apply equally to the uses of the invention.

It will be understood that the use of the kit is particularly intended for the predictive method and methods of personalised medicine of the invention.

4. Therapeutic Uses of the Invention

In another aspect, the invention relates to MSCs for use in the treatment of an immune-mediated inflammatory disease in a patient in need thereof, wherein the patient has an increased level of monocytes in respect to a reference value, and/or a decreased level of $T_{reg}$ cells in respect to a reference value, and/or the ratio of CD4+ T cells to $T_{reg}$ cells (CD4+/$T_{reg}$) in respect to a reference value, and/or the T cell proliferation capacity in a sample containing T-cells from said patient after in vitro culture in the presence of MSCs, in respect to a reference value.

Alternatively, this aspect may be reformulated as the use of MSCs for the manufacture of a medicament for the treatment of an immune-mediated inflammatory disease in a patient in need thereof, wherein the patient has an increased level of monocytes in respect to a reference value, and/or a decreased level of $T_{reg}$ cells in respect to a reference value, and/or an increased ratio of CD4+ T cells to $T_{reg}$ cells (CD4+/$T_{reg}$) in respect to a reference value, and/or an increased T cell proliferation capacity in a sample containing T-cells from said patient after in vitro culture in the presence of MSCs in respect to a reference value. Alternatively, this aspect may also be reformulated as a method of treatment of an immune-mediated inflammatory disease in a patient in need thereof, comprising the administration of MSCs to said patient, wherein the patient has an increased level of monocytes in respect to a reference value, and/or a decreased level of $T_{reg}$ cells in respect to a reference value, and/or an increased ratio of CD4+ T cells to $T_{reg}$ cells (CD4+/$T_{reg}$) in respect to a reference value, and/or an increased T cell proliferation capacity in a sample containing T-cells from said patient after in vitro culture in the presence of MSCs in respect to a reference value.

The definitions and particular embodiments relating to the terms "therapy", "patient", "immune-mediated inflammatory disease", and "reference value" have been described in detail in the context of the predictive method of the invention and apply equally to the therapeutic uses of the invention.

It will be immediately apparent that this aspect of the invention is based on a patient that has been identified by the predictive method of the invention. Therefore, the particular and preferred embodiments of the predictive method of the invention are also included here by reference.

Additional aspects of the invention include:
 Use of a kit according to the invention, said kit further comprising MSCs.
 The predictive method of the invention, or the first or second, methods of personalised medicine of the invention, or the use of the kit according to the invention, or the MSCs for use according to the invention, wherein the MSCs or the therapy based on MSCs are administered via the rectal, nasal, buccal, vaginal, subcutaneous, intracutaneous, intravenous, intraperitoneal, intramuscular, intraarticular, intrasynovial, intrasternal, intrathecal, intralesional, or intracranial route, or via an implanted reservoir.
 The predictive method of the invention, or the first or second methods of personalised medicine of the invention, or the use of the kit according to the invention, or the MSCs for use according to the invention, wherein the level of monocytes, and/or the level of $T_{reg}$ cells, and/or the ratio of CD4+ T cells to $T_{reg}$ cells (CD4+/$T_{reg}$) in respect to a reference value, and/or the T cell proliferation capacity is determined by an immunological technique selected from the group consisting of flow cytometry, ELISA, and beads-based techniques.

Various embodiments of the invention will be illustrated by the following examples, which are to be taken to illustrate but not to limit the invention described herein.

EXAMPLES

Materials and Methods
Patient Study Design and Treatments

A multicenter, single blind, fixed dose escalation, three treatment groups, placebo-controlled phase Ib/IIa clinical trial, with a follow-up period of up to 6 months after the administration of the first dose of treatment (EudraCT no.: 2010-021602-37).

The study medication consisted of expanded adipose derived stem cells (eASCs) extracted from liposuction, and administered as an intravenous (IV) infusion after suspension in Ringer's lactate solution. Forty-six patients received eASCs and 7 patients received a placebo. The placebo arm consisted of Ringer's lactate solution.

Eleven patients treated with eASCs were selected as good responders to the ASC administration based on the results of MRI at the end of the study (RAMRIS) and and/or EULAR responder moderate or good response (at any time) and named "responders". The remaining 35 patients that, according to the criteria, were less responsive to the treatment with eASCs were named as "rest of the population".

Reagents and Antibodies

5(6)-Carboxyfluorescein diacetate N-Succinimidyl Ester (CFSE) was from Sigma-Aldrich (St. Louis, Mo.). Pan T cell Activation kit (antiCD3, CD2, CD28 coated beads) was from Milteny Biotech (Bergisch Gladbach, Germany). Anti-CD3, CD4, CD8, CD14, CD20, CD25, CD69 HLA-DR and FOXP3 antibodies and 7-amino-actinomycin D (7-AAD) were from Becton Dickinson (San Diego, Calif.).

eASCs and Peripheral Blood Mononuclear Cells

Human adipose tissue aspirates from healthy donors were processed as described elsewhere. The allogeneic eASCs medicinal product consists of a cellular suspension of living adult stem cells of mesenchymal origin extracted from the subdermal adipose tissue of healthy donors. Subdermal adipose tissue was liposuctioned from healthy donors and transported to the manufacturing facility. The donation, procurement, and testing were carried out according to the requirements of Directive 2004/23/EC and therefore under Directives 2006/17/EC and 2006/83/EC. ASCs were isolated by digesting the adipose tissue with type I collagenase, followed by centrifugation. The cell pellet obtained was resuspended and lysed in erythrocyte lysis solution and centrifuged. The stromal vascular fraction, resulting from the cell pellet, was placed in cell culture containers in culture medium and antibiotics, and incubated at 37° C. and 5% $CO_2$ and in a humidified atmosphere. At 24-48 h postplating, the culture medium was removed to eliminate the non-attached cell fraction. ASCs adhered to the plastic culture plates that were expanded under in vitro conditions. Every 3-4 days, the culture medium was changed after reaching 90-95% confluence, and cells were detached with trypsin/EDTA, collected, centrifuged, and expanded without antibiotics to the required duplication. They were then harvested and cryopreserved until use. Before the appointed administration date, sufficient cryopreserved vials were thawed to provide the required dose for administration. All the eASCs used were fulfilling the release criteria of identity, purity and potency needed for their clinical use.

Peripheral blood mononuclear cells (PBMC) were isolated from buffy coats kindly provided by the National Transfusion Centre of the Comunidad AutOnoma of Madrid, Spain using Ficoll-paque Plus (GE Healthcare Biosciences AB, Uppsala, Sweden) following the supplier's protocol. Briefly, blood samples were diluted with balanced salt solution and Ficoll was added to create a density gradient. After centrifugation, the interface containing mononuclear cells was gently collected.

EDTA-blood was collected from the patients immediately before the infusions of eASCs at the start, at 4 and at 12 weeks after the first eASC or placebo administration. A fraction of total blood was selected for multiparametric cell analysis by flow cytometry. T cells (CD3$^+$), helper T cells CD4$^+$CD3$^+$, cytotoxic T cells CD8$^+$CD3$^+$, regulatory T cells (CD3$^+$CD4$^+$CD25$^+$foxp3$^+$), NK cells (CD16$^+$CD56$^+$), B cells (CD20$^+$), and monocytes (CD14$^+$) were studied. The rest of the blood was centrifuged and the plasma was collected and stored for further use. The cellular pellet was processed for PBMC isolation by Ficoll gradient centrifugation (Histopaque 1077; Sigma-Aldrich Corp, St Louis, Mo.). The cells were then washed three times with phosphate buffered saline (PBS) and stored until use.

Plasma Levels of Soluble Mediators

Magnetic Beads from Affymetrix were used in plasma samples collected in EDTA tubes to perform quantitative, multiplexed immunoassays based on the Luminex® xMAP® technology for simultaneous measurements of multiple protein biomarkers. Fifteen inflammatory mediators (IL1-b, sIL-1RA, IL-2, IL4, IL-6, IL-8, IL10, IL12p70, IL17-A, IL23, IFN-γ, TNF-α, IFN-α, TGF-β and sCD-40L) were selected for the study. Plasma samples that were analysed for TGFβ were acidified with of 1N HCl incubated for 10 min at 37° C. and further neutralised by adding 1.2N NaOH/0.5M HEPES. The assay was performed following manufacturer instructions (Procarta® Immunoassay from Affymetrix).

Lymphocyte Proliferation Assays

The assay was performed in 96-well, flat-bottom plates. PMBCs both from healthy donors and RA patients were labelled with CFSE and further seeded at 2×10$^5$/well in RPMI (Roswell Park Memorial Institute) tissue culture medium containing 10% FCS, glutamine, and penicillin-streptomycin (Biological Industries) and stimulated with the anti CD3+CD2+CD28 coated beads (Mylteny Biotech). Cells were cultured in the presence or absence of eASCs (4×10$^3$ eASCs per each 2×10$^5$ PBMCs, ratio 1:50) for 120 hours in a humidified atmosphere of 5% $CO_2$ at 37° C. Cells were harvested and proliferation was measured by CFSE dilution analysis. FCSExpress software was used for calculating the Division Index (Division Index: average number of cells that a dividing cell became. N is the number of cells in a generation. $^{P-1}_{i=1}\Sigma N_i / ^{P-1}_{i=1}\Sigma N_i/2_i$, where i=the corresponding generation number; P=the total number of peaks found). The percentage of proliferation was also calculated, based on the normalisation to the maximum proliferation that activated PBMCs can reach.

Modification of Activation Markers on T Cells Upon eASC Recall

The expression of CD69 and HLA-DR activation markers were measured in Patient's T cells before treatment. Furthermore PBMCs were left on resting overnight in contact or not with eASCs for 24 hours in the absence of any stimulation. Surface expression of CD69 and HLA-DR was again analysed on gated CD3+ T cell population. The expression of both activation markers was compared in samples cultured in the absence and presence of eASCs.

Statistical Analysis

Variables were presented as the interquartile range (p75 upper edge, p25 lower edge, p50 midline), p95 (line above the box), and p5 (line below the box) as a non-normal distribution. Non-parametric techniques (Mann-Whitney U test) were used to compare distribution between two groups. The correlation between continuous variables (dose and percentage of inhibition of the proliferation) was determined using the Spearman test.

Example 1: Cell Distribution and Plasma Cytokines in Peripheral Blood

Peripheral blood cells were obtained from the 53 patients enrolled in the trial at baseline and at 4 and 12 weeks after first eASC or placebo administration. The percentage of T cells (CD3+), Th cells (CD3+CD4+), Tc cells (CD3+CD8+), NK cells (CD3-CD56+), B cells (CD20+), monocytes (CD14+) and $T_{reg}$ cells (CD4+CD25b+FOXP3+) were measured and compared between placebo and eASC treated patients (FIG. 1).

Results showed no significant alterations in the T cell population (nor CD4 or CD8) after ASC or placebo administration. Similarly the percentage of NK cells and B cells did not show any modification after the treatment both in placebo and eASC groups. Remarkable alterations in the monocyte population were observed: monocytes increased at W4 and decrease at W12 in the placebo group, whereas in the eASC treated group the decrease of monocytes was maintained along W4 and W12. Interestingly, the $T_{reg}$ compartment was significantly reduced in the treated group at W12 compared with baseline (p=0.018) and no changes were found in the placebo group (FIG. 1).

Figure 2:
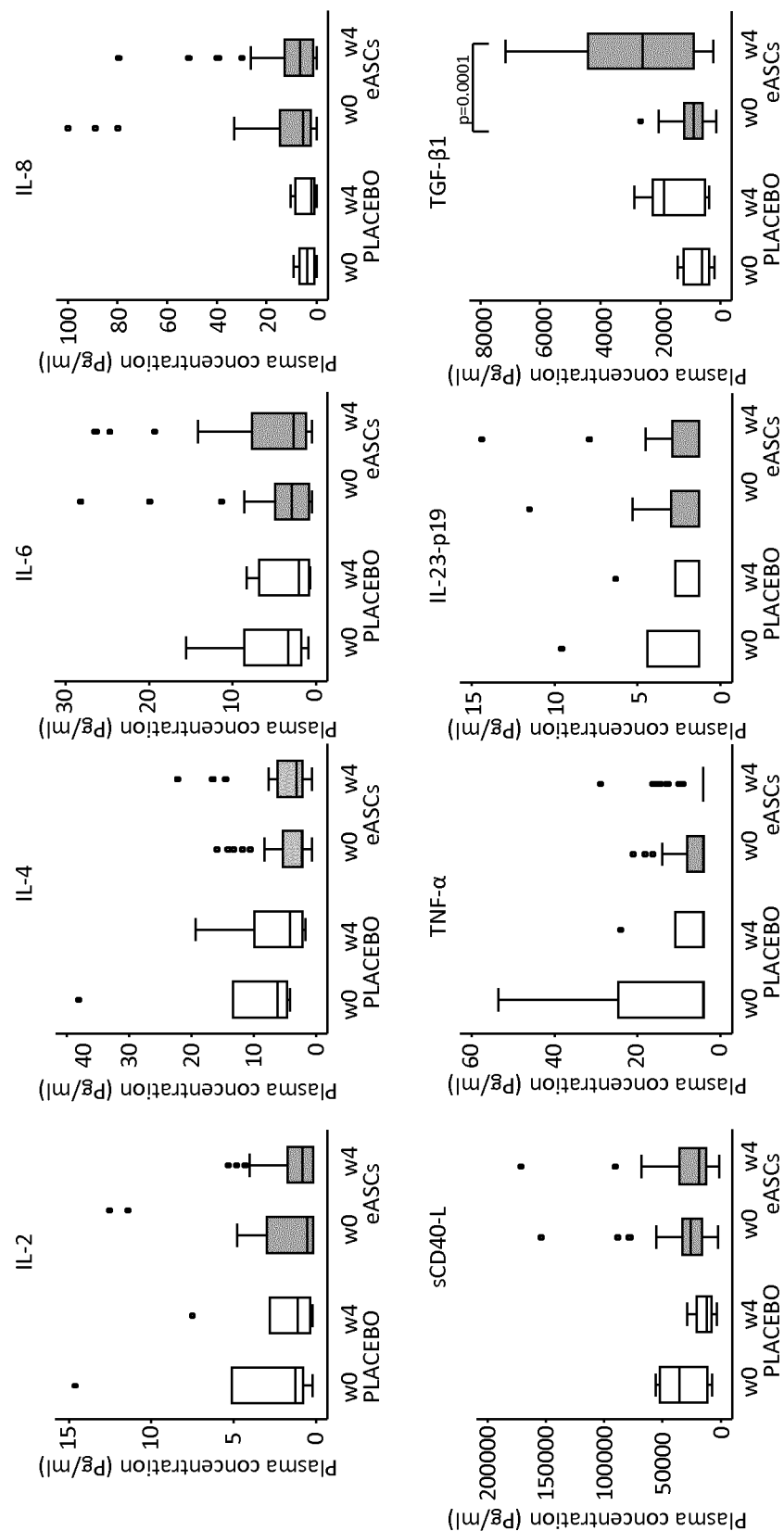
FIG. 2.—Plasma levels of cytokines in peripheral blood in eASC treated and placebo groups.—Plasma from patients was selected at baseline and week 4 after expanded adipose derived stem cells (eASC) or placebo administration for determination of the concentration (in pg/ml) of the cytokines: IL-2, IL4, IL-6, IL-8, sCD-40L, TNF-α, IL-23p19 and TGF-β). All data are presented as the interquartile range (p75 upper edge, p25 lower edge, p50 midline), p95 (line above the box), and p5 (line below the box) of the different immunological parameters. Dots represent the outliers. Significance was analysed by the Mann-Whitney test.

Plasma from patients at baseline and week 4 were used for the analysis of soluble factors. A panel of inflammatory mediators (IL1-b, sIL-1RA, IL-2, IL-4, IL-6, IL-8, IL-10, IL-12p70, IL-17, IL-23, IFN-γ, TNF-α, IFN-α, TGF-β, and sCD-40 L) was measured. Results indicated that the concentration of several cytokines was very close to the limit of detection (i.e. IFN-γ, IL-10, IL-12-p70, IL-17, IFN-α, IL-1β, IL-1Rα) and comparisons were not reliable. Interestingly, TGF-β levels showed a statistically significant increase at week 4 compared to baseline in eASCs treated group (p<0.001) (FIG. 2). No significant differences were found between baseline and week 4, nor in the placebo or in the eASC group for the other cytokines measured.

Figure 3:
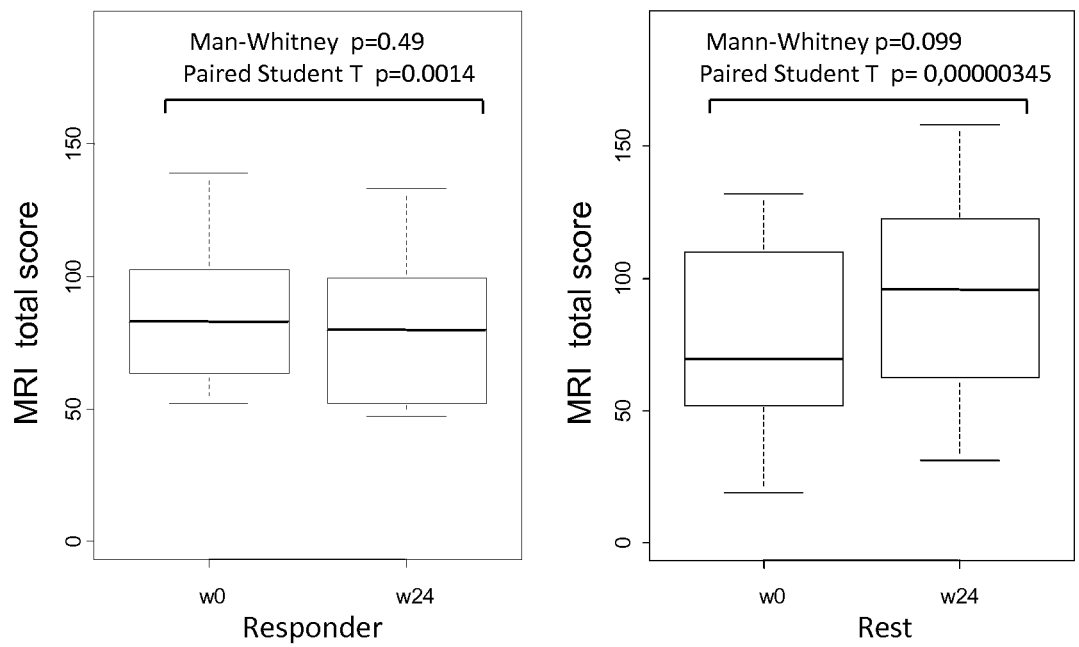
FIG. 3.—Patient stratification between responders and rest of the population.—A) RAMRIS total score in "responders" and "rest of the population". Values of patients at baseline (week 0) and end of study (week 24) were used in this figure. Box plots show the interquartile range (p75 upper edge, p25 lower edge, p50 midline), p95 (line above the box), and p5 (line below the box); single dots represent outliers. Subgroups were stratified on the basis of a control or reduction of the RAMRIS score for the "responders" group and an increase of the RAMRIS total score for the "rest of the population" group. Significance was analysed by the Mann-Whitney test and Student T Test for paired samples. B) EULAR response (DAS28-CRP) in "responders" and "rest of the population". Values of patients at baseline (week 0) and weeks 4, 5 and 6 after eASCs administration were used in this figure. Subgroups were stratified on the basis of the RAMRIS score at the end of the study. Box plots show the interquartile range (p75 upper edge, p25 lower edge, p50 midline), p95 (line above the box), and p5 (line below the box); single dots represent outliers. Significance was analysed by the Mann-Whitney test.
Figure 3:
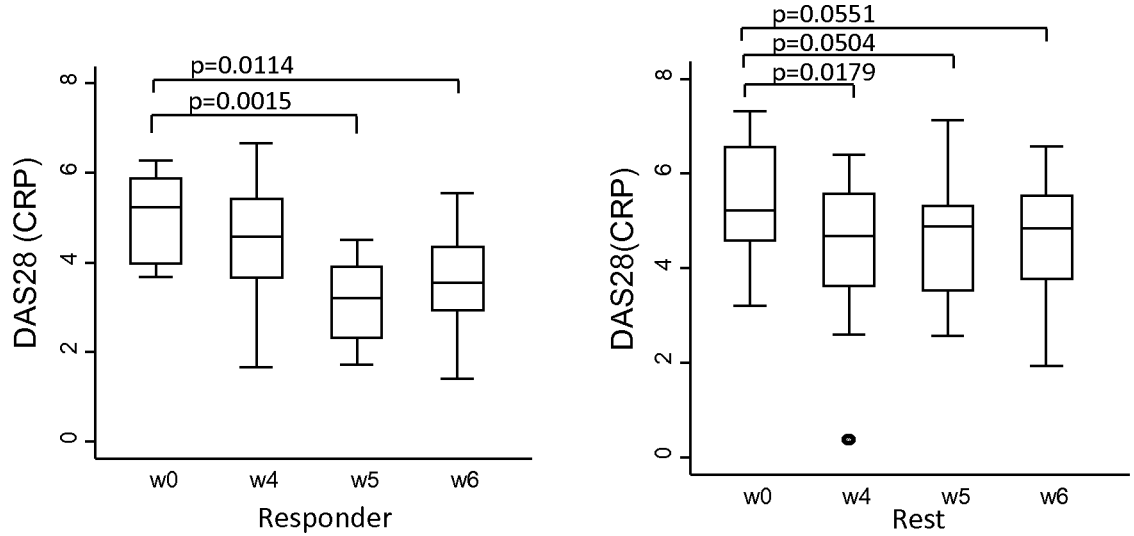
Figure 4:
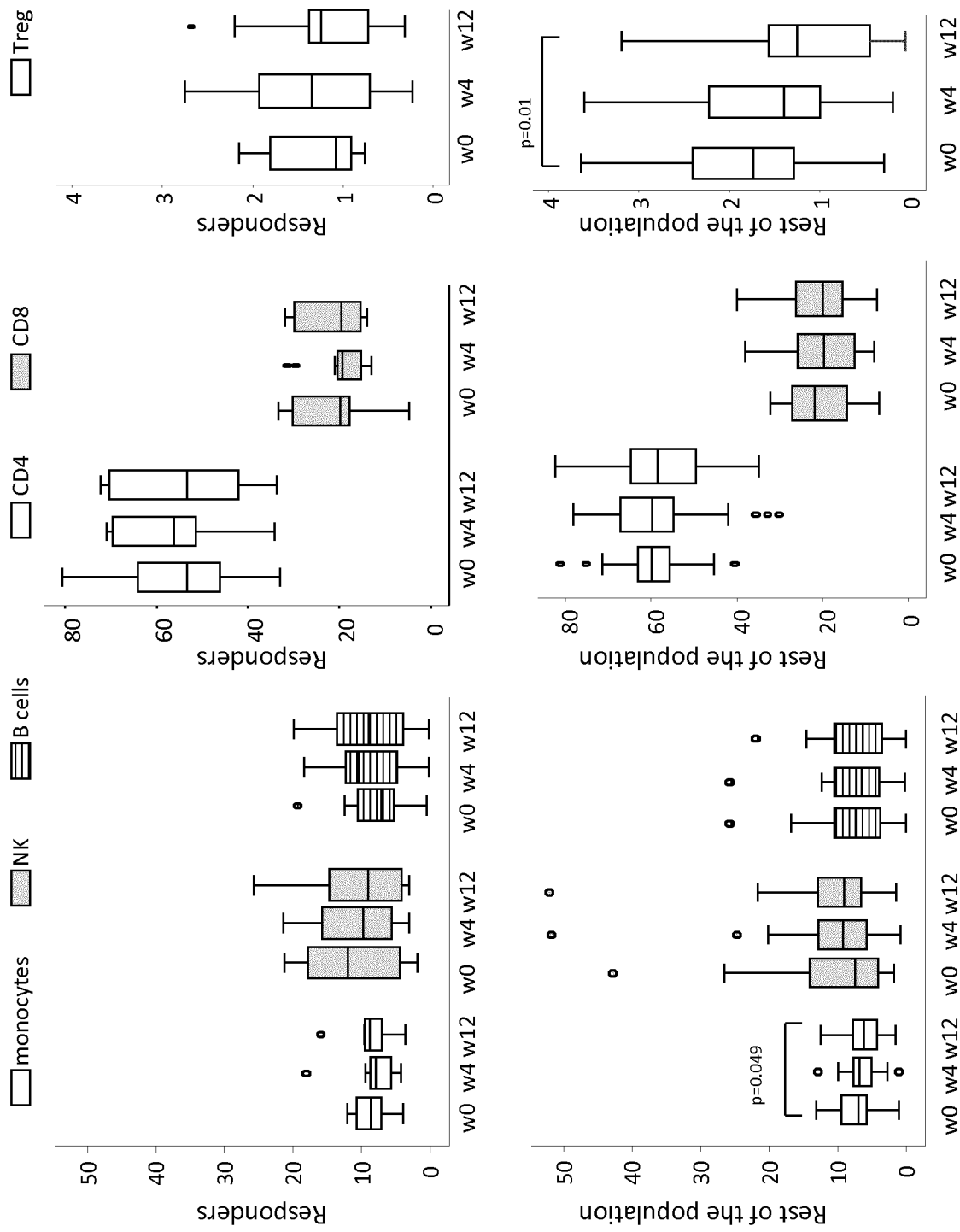
FIG. 4.—Cell distribution in responder patients and rest of the population.—Percentage of positive cells at baseline (week 0), week 4 and week 12 after ASC or placebo administration is shown. T cells (CD3/CD4/CD8), NK cells (CD56+), B cells (CD20+), monocytes (CD14+) and $T_{reg}$ cells (CD4+CD25+FoxP3+) were analysed in responders and rest of the population. Data are presented as the interquartile range (p75 upper edge, p25 lower edge, p50 midline), p95 (line above the box), and p5 (line below the box) of the different immunological parameters. Dots represent the outliers. Significance was analysed by the Mann-Whitney test.

Example 2: Study in Responder and Rest of the Population: Circulating Cells and Plasma Cytokines The 46 patients treated with eASCs were divided in two groups based on the results of MRI at the end of the study (RAMRIS) and/or EULAR responder moderate or good response at any time (FIG. 3). Among them, 11 patients had a positive clinical response upon eASC treatment and were named "responder" group. The rest of eASC-treated patients were named "rest of the population" and served as controls. The circulating T cells (both CD4+ and CD8+), NK cells, monocytes and $T_{regs}$, remained stable upon visits in the responder population and only an trend to an increase of the median values of $T_{reg}$ cells could be observed, whereas in the "rest of the population" a significant reduction in monocytes at W4 (p=0.0497) and in $T_{regs}$ at W12 (p=0.0108) was found (FIG. 4).

Figure 5:
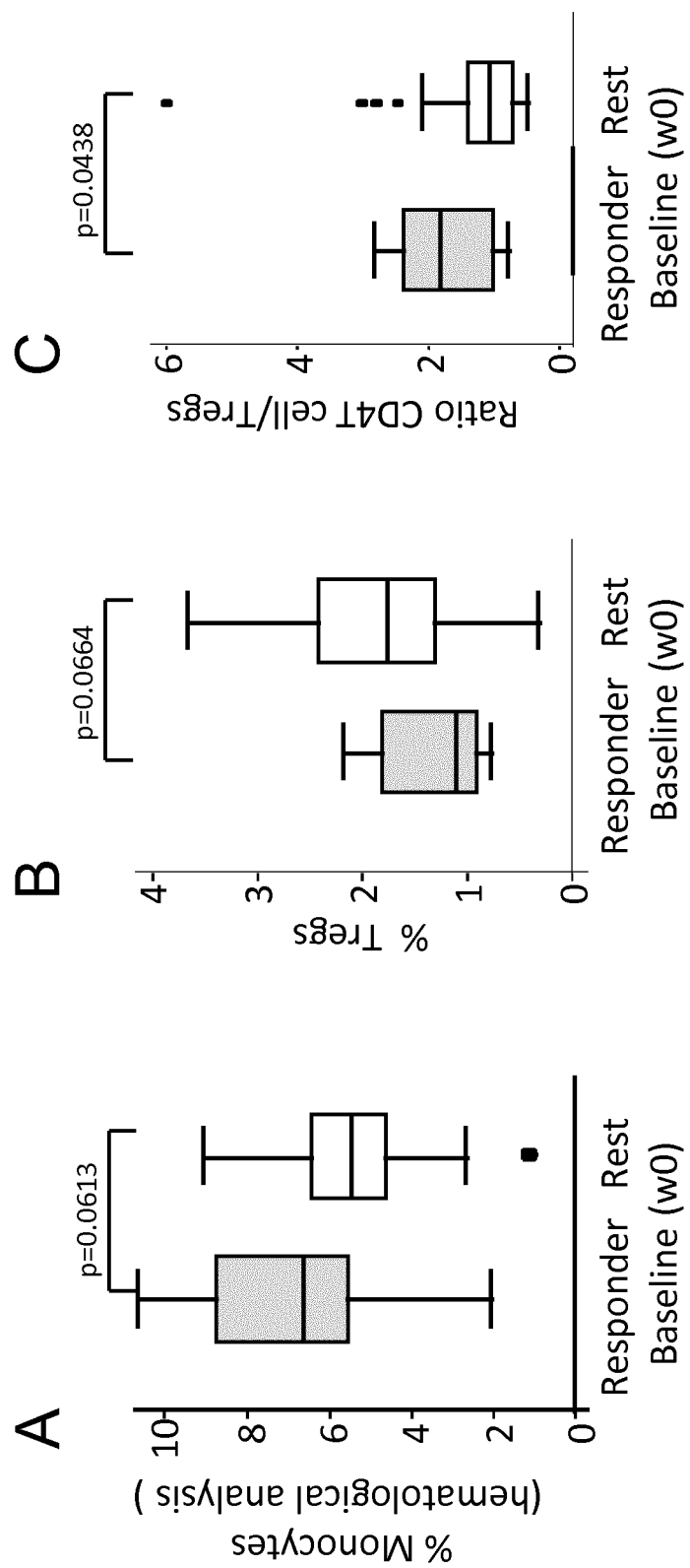
FIG. 5.—Cell distribution in responder patients and rest of the population.—Baseline levels (week 0) of (A) monocytes, (B) $T_{regs}$ and (C) ratio CD4+ T cell/$T_{regs}$ in "responders" and "rest of the population". Data are presented as the interquartile range (p75 upper edge, p25 lower edge, p50 midline), p95 (line above the box), and p5 (line below the box) of the different immunological parameters. Dots represent the outliers. Significance was analysed by the Mann-Whitney test.

Interestingly, baseline levels of two cell subsets in circulation were different between the "responders" and the "rest of the population": "Responder" patients had a higher frequency of monocytes and lower frequency of $T_{regs}$ than the "rest of the population" (FIG. 5). Furthermore, the calculation of the CD4$^+$ cells/$T_{reg}$ cells ratio enhanced that difference, showing that the number of $T_{regs}$ relative to the CD4 cells was significantly lower in the "responder" group (p=0.0438). This indicates that the "responder" population has a different baseline immune status associated with lower $T_{regs}$ and higher monocytes.

Figure 6:
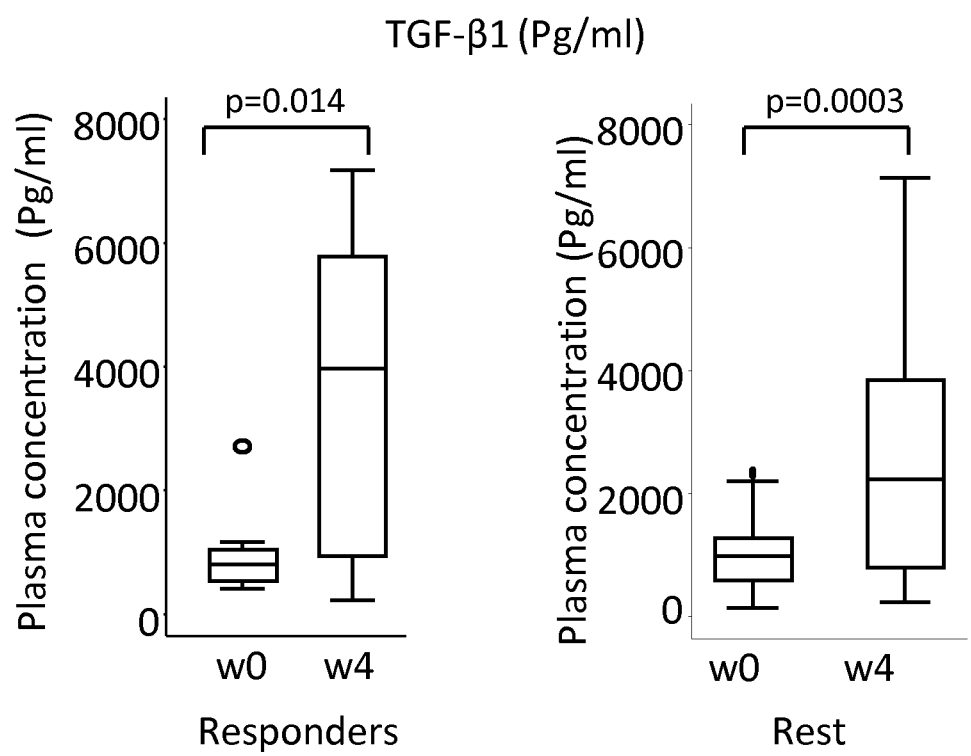
FIG. 6.—TGF-β levels in responder patients and rest of the population.—TGF-β concentration in pg/ml was analysed in responder patients and rest of the population at baseline (week 0) and week 4. Results are grouped in responders (n=11) and rest of the population (n=35). Data are presented as the interquartile range (p75 upper edge, p25 lower edge, p50 midline), p95 (line above the box), and p5 (line below the box) of the different immunological parameters. Dots represent the outliers. Significance was analysed by the Mann-Whitney test.

Plasma level of TGF-β was significantly increased after treatment both in the "responder" group and in the "rest of the population", suggesting that TGF-β is not directly linked to the clinical response but is a consequence of the eASCs administration (FIG. 6). No statistically significant differences were found between baseline and W4 in the rest of the cytokines measured.

Example 3: Proliferative Capacity of T Cells In Vitro

Figure 7:
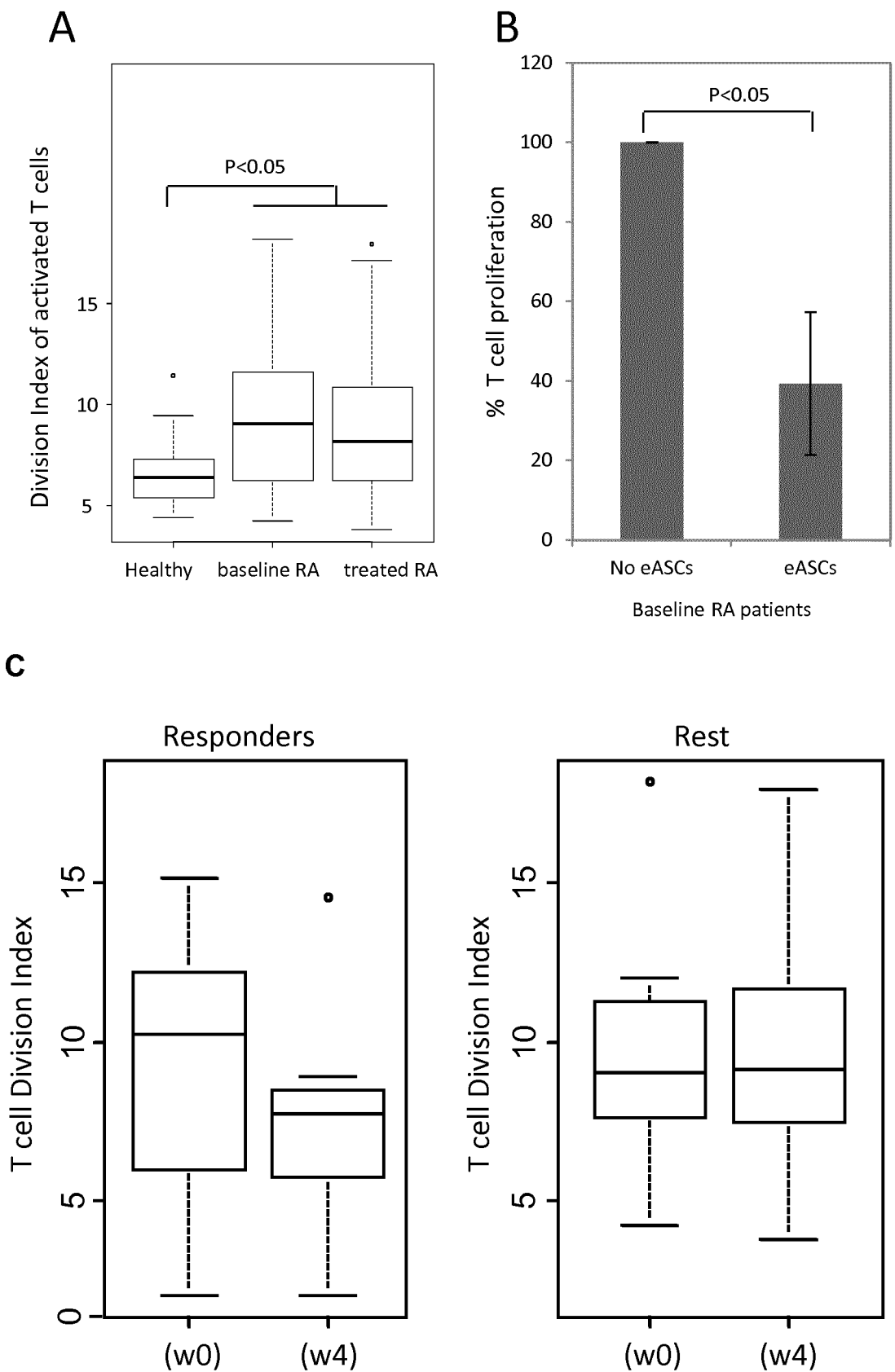
FIG. 7.—T cell proliferation capacity and eASC inhibitory capacity in RA patients.—A) Proliferation studies were done in PBMCs from patients at baseline (week 0) and at week 4. PBMCs were activated with beads coated with anti CD3/CD2/CD28 and incubated during 120 hours. Division index is representing the proliferative capacity of activated T cells from healthy PBMCs, non-treated RA patients and from RA patients 4 weeks after first administration of allogeneic ASCs. B) Proliferation studies were done in PBMCs from patients at baseline (week 0) in the presence and absence of eASCs. Results show the percentage of T cell proliferation upon activation in the absence and presence of eASCs normalised to the maximum proliferation calculated for PBMCs alone. Bar graph represents mean and standard deviation of the percentage of proliferation at baseline in RA patients. C) Proliferation studies were done in PBMCs from patients at baseline (week 0) and week 4 after eASC administration. PBMCs were activated with beads coated with anti CD3/CD2/CD28 and incubated during 120 hours. T cell division index is representing the proliferative capacity of activated T cells in "responders" and "rest of the population". Box plots show the interquartile range (p75 upper edge, p25 lower edge, p50 midline), p95 (line above the box), and p5 (line below the box). Significance was analysed by the Mann-Whitney test.

T cell proliferative capacity upon stimulation was tested in the RA population at baseline and after treatment (week 4) and compared to healthy controls. CFSE labelled PBMCs were cultured in the presence of anti CD3/CD2/CD28 coated beads during 120 hours and T cell proliferation was measured by CFSE tracking analysis. Results indicated that the Division Index (D.I.) of patient's T cells was significantly higher than in the healthy controls (p=0.031) (FIG. 7A). It is interesting to mention that there is a much higher heterogeneity in the values obtained from the RA group than in the values from healthy volunteers, showing that T cell function is not homogeneous in this refractory patient population. In addition, we did demonstrate that the proliferative capacity of patient's T cells was comparable before and after eASC treatment, indicating that no modification of the T cell proliferative capacity as a consequence of the eASCs treatment could be seen. Furthermore, we aimed to study whether T cells from RA patients were susceptible of the eASCs antiproliferative effect in vitro; to address that, baseline patients' PBMCs were CFSE labelled, stimulated and cultured in the presence or absence of eASCs. Results indicated that T cell proliferation was significantly inhibited when eASCs were present in the cultures, demonstrating that although no apparent modification of the T cell proliferative capacity after treatment, patient's T cells were responsive to the in vitro action of eASCs (FIG. 7B).

Interestingly, the comparison between "responders" and "rest of the population" resulted in a clear indication of a decrease in the proliferation of "responder" T cells after eASCs treatment (no statistically significant), whereas the D.I was not modified in the "rest of the population" (FIG. 7C). It is also important to remark that at baseline, the proliferative capacity of the "responder" T cells tended to be higher than the "rest of the population".

The invention claimed is:

1. A method for selecting and treating a patient suffering from an immune-mediated inflammatory disease, the method comprising:
    (a) obtaining a blood sample from a patient;
    (b) determining in said sample from the patient at least one parameter selected from the group consisting of:
        (i) the level of monocytes,
        (ii) the level of $T_{reg}$ cells,
        (iii) the ratio of CD4+ T cells to $T_{reg}$ cells (CD4+/$T_{reg}$), and
        (iv) the T cell proliferation capacity,
    (c) comparing the parameters in said sample with their reference values;
    (d) selecting a patient as likely to show a clinical response to a therapy comprising the administration of mesenchymal stem cells (MSCs) wherein the patient has at least one parameter selected from the group consisting of:
        an increased level of monocytes in said sample with respect to a reference value, wherein the reference value is obtained from the value of the level of monocytes in a blood sample from one or more patients who do not respond to a therapy based on comprising the administration of MSCs,
        a decreased level of $T_{reg}$ cells with respect to a reference value, wherein the reference value is obtained from the value of the level of $T_{reg}$ cells in a blood sample from one or more patients who do not respond to a therapy comprising the administration of MSCs,
        an increased ratio of CD4+ T cells to $T_{reg}$ cells (CD4+/$T_{reg}$) with respect to a reference value, wherein the reference value is obtained from the value of the ratio of CD4+ T cells to $T_{reg}$ cells (CD4+/$T_{reg}$) in a blood sample from one or more patients who do not respond to a therapy comprising the administration of MSCs, and
        an increased T cell proliferation capacity with respect to a reference value,
    wherein the reference value is obtained from the value of the T cell proliferation capacity in a blood sample from one or more patients who do not respond to a therapy comprising the administration of MSCs; and
    (e) administering a therapy comprising the administration of MSCs to the patient selected in step (d) as likely to show a clinical response to the therapy.

2. The method according to claim 1, wherein said immune-mediated inflammatory disease is rheumatoid arthritis.

3. The method according to claim 2, wherein said rheumatoid arthritis is refractory.

4. The method according to claim 1, wherein the MSCs are allogeneic stem cells.

5. The method according to claim 4, wherein the stem cells are adipose tissue derived stromal stem cells (ASCs).

6. The method according to claim 5, wherein the ASCs are expanded ASCs.

7. The method according to claim 1, wherein administration of MSCs is intravenous.

8. A method for the treatment of an immune-mediated inflammatory disease in a patient in need thereof, the method comprising the steps of:
    (a) selecting a patient having at least one parameter selected from the group consisting of:
        an increased level of monocytes with respect to a reference value, wherein the reference value is obtained from the value of the level of monocytes in a blood sample from one or more patients who do not respond to a therapy comprising the administration of MSCs,
        a decreased level of $T_{reg}$ cells with respect to a reference value, wherein the reference value is obtained from the value of the level of Treg cells in a blood sample from one or more patients who do not respond to a therapy comprising the administration of MSCs,
        an increased CD4+/$T_{reg}$ ratio with respect to a reference value, wherein the reference value is obtained from the value of the ratio of CD4+ T cells to $T_{reg}$ cells (CD4+/$T_{reg}$) in a blood sample from one or more patients who do not respond to a therapy comprising the administration of MSCs, and
        an increased T cell proliferation capacity with respect to a reference value, wherein the reference value is obtained from the value of the T cell proliferation capacity in a blood sample from one or more patients who do not respond to a therapy comprising the administration of MSCs; and (b) administering MSCs to the patient selected in step (a).

9. The method according to claim 8, wherein the MSCs are allogeneic stem cells.

10. The method according to claim 8, wherein the stem cells are adipose tissue derived stromal stem cells (ASCs).

11. The method according to claim 10, wherein the ASCs are expanded ASCs.

12. The method according to claim 8, wherein the MSCs are administered systemically or locally.

13. The method according to claim 8, wherein said immune-mediated inflammatory disease is rheumatoid arthritis.

14. The method according to claim 13, wherein said rheumatoid arthritis is refractory.

15. The method according to claim 14, wherein the patient is refractory to at least one biological treatment.

16. The method according to claim 15, wherein said at least one biological treatment is a TNF-α inhibitor, IL-1 inhibitor, IL-6 inhibitor, or T cell-costimulation inhibitor, or an anti-CD20 antibody.

17. The method according to claim 16, wherein:
the TNF-α inhibitor is Adalimumab, Certolizumab, Etanercept, Golimumab, Rituximab, or Infliximab; the IL-1 inhibitor is anakinra; the IL-6 inhibitor is tocilizumab; the T cell-costimulation inhibitor is Abatacept; and the anti-CD20 antibody is rituximab.

* * * * *